United States Patent
Hayashi et al.

(10) Patent No.: US 8,629,397 B2
(45) Date of Patent: Jan. 14, 2014

(54) SPECTROPHOTOMETER AND METHOD FOR CALIBRATING THE SAME

(75) Inventors: Daisuke Hayashi, Otsu (JP); Katsumi Nishimura, Kyoto (JP)

(73) Assignee: Horiba STEC, Co., Ltd., Kyoto-shi (JP)

( * ) Notice: Subject to any disclaimer, the term of this patent is extended or adjusted under 35 U.S.C. 154(b) by 114 days.

(21) Appl. No.: 13/431,718

(22) Filed: Mar. 27, 2012

(65) Prior Publication Data

US 2012/0250014 A1    Oct. 4, 2012

(30) Foreign Application Priority Data

Mar. 28, 2011 (JP) ................................. 2011-069808

(51) Int. Cl.
*G01J 5/00* (2006.01)
(52) U.S. Cl.
USPC ....................................................... 250/338.1
(58) Field of Classification Search
USPC .................... 250/338.1–338.5, 340
See application file for complete search history.

(56) References Cited

U.S. PATENT DOCUMENTS

| | | | | |
|---|---|---|---|---|
| 3,781,910 A | * | 12/1973 | Herrmann | 250/341.5 |
| 5,206,511 A | * | 4/1993 | Apperson et al. | 250/343 |
| 5,457,320 A | * | 10/1995 | Eckles et al. | 250/345 |
| 6,274,879 B1 | * | 8/2001 | Best-Timmann | 250/573 |

FOREIGN PATENT DOCUMENTS

| | | |
|---|---|---|
| JP | 2000241346 A | 9/2000 |
| JP | 2005257358 A | 9/2005 |

* cited by examiner

*Primary Examiner* — Kiho Kim
(74) *Attorney, Agent, or Firm* — Alleman Hall McCoy Russell & Tuttle LLP

(57) ABSTRACT

A spectrophotometer is provided, including a light source for irradiating light into a sample gas, a photodetector for detecting light transmitted through the sample gas, an optical filter, and an operation device for calculating a concentration of an actual gas to be measured, contained in the sample gas based on a detection signal value obtained from the photodetector. The operation device calculates the concentration of the actual gas based on function $\alpha$ for associating a concentration of a substitute gas with the actual gas obtained from a reference instrument, function $\beta$ for associating a relation between a light absorption of the actual gas and the substitute gas in the reference instrument, with a relation between a light absorption of the actual gas the substitute gas in a calibration instrument, and a function indicating a relation between the concentration of the substitute gas and the detection signal value.

3 Claims, 6 Drawing Sheets

SPECTROPHOTOMETER AND METHOD FOR CALIBRATING THE SAME

BACKGROUND

The present invention relates to a spectrophotometer and a method of calibrating the same.

Although various kinds of spectrophotometers are known to perform quantitative analysis and qualitative analysis of a specimen by obtaining an absorbed spectrum of a material contained in the specimen which is a measurement target, as infrared spectrophotometers, there exist, for example, a dispersive infrared spectrophotometer (dispersive IR), a Fourier transform infrared spectrophotometer (FTIR), a non-dispersive infrared spectrophotometer (NDIR), among which the non-dispersive infrared spectrophotometer (NDIR) selects an infrared absorbing wavelength of a specimen by using a bandpass filter with multi-layer films (see JP2000-241346A and JP2005-257358A).

Before an NDIR is shipped out, an initial concentration calibration, that is, a concentration of gas and an infrared light absorption are associated with each other therein. Specifically, first, among NDIRs with the same specification, an instrument body to serve as a reference (hereinafter, may be "reference instrument") is selected, and with this reference instrument, an equation expressing a relation between an actual gas concentration $C_{actual\_gas}$ and a photo detection signal value x, obtained from a photodetector, is obtained ($C_{actual\_gas} = g_{reference\_instrument}(x)$) using the actual gas that is a measurement target. Further, the actual gas is changed to a substitute gas, and an equation expressing a relation between a substitute gas concentration $C_{substitute\_gas}$ and the photo detection signal value x, obtained from the photodetector, is obtained ($C_{substitute\_gas} = f_{reference\_instrument}(x)$) as well. Thus, based on these equations, a conversion coefficient $\alpha$ with which the substitute gas concentration $C_{substitute\_gas}$ is converted into the actual gas concentration $C_{actual\_gas}$ is obtained.

Next, with an arbitrary instrument body to be calibrated (hereinafter, may be "calibration instrument"), an equation expressing a relation between the substitute gas concentration $C_{substitute\_gas}$ and the photo detection signal value x, obtained from the photodetector, is obtained ($C_{substitute\_gas} = f_{calibration\_instrument}(x)$) using the substitute gas.

Further, under an assumption in which a ratio in infrared light absorption between the actual gas and the substitute gas ($\text{abs.}_{actual\_gas}/\text{abs.}_{substitute\_gas}$) is constant with any instrument bodies, according to the conversion coefficient $\alpha$ obtained from the reference instrument and the equation expressing the relation between the substitute gas concentration $C_{substitute\_gas}$ obtained from the calibration instrument and the photo detection signal value x ($C_{substitute\_gas} = f_{reference\_instrument}(x)$), an equation for calculating the actual gas concentration $C_{actual\_gas}$ for the calibration instrument ($C_{actual\_gas} = \alpha \times f_{calibration\_instrument}(x)$) is obtained. Although, with the reference instrument, as described above, $C = g(x)$ is the function for calculating the actual gas concentration and $C = f(x)$ is the function for calculating the substitute gas concentration, in calculating the actual gas concentration in the calibration instrument, $C = \alpha \times f(x)$ is used, and the photo detection signal value for a case where the actual gas is adopted for the calibration instrument is substituted as x therein.

Related Art Documents

Patent Documents

[Patent Document 1] JP2000-241346A
[Patent Document 2] JP2005-257358A

However, it has become clear that the measurement results vary among the instrument bodies in which the initial concentration calibration had been performed as above. Supposedly if the actual gas is adopted for all the calibration instruments and a conversion coefficient $\alpha_{calibration\_instrument}$ is calculated individually, the problem of such a variation can be solved; however, in practice, many kinds of the actual gas to serve as the measurement target are difficult to be used for reasons of, for example, the actual gas being poisonous, therefore, in calibration, there is no choice but to use the harmless substitute gas instead of the actual gas.

Thus, the present invention is to provide a spectrophotometer in which an instrumental difference among the instrument bodies is eliminated, and a method of calibrating is the same.

Means for Solving the Problems

As a result of committed studies by the present inventors, they have found that a ratio in infrared light absorption between an actual gas and a substitute gas ($\text{abs.}_{actual\_gas}actual\_gas/\text{abs.}_{substitute\_gas}$) varies in each instrument body, and further, have clarified that this instrumental difference is caused by a difference in optical property of a bandpass filter (see FIG. 5). The present invention is accomplished based on such a perception.

That is, a spectrophotometer according to one aspect of the invention includes a light source for irradiating light into a sample gas, a photodetector for detecting light transmitted through the sample gas, an optical filter arranged between the light source and the photodetector, and an operation device for calculating a concentration of an actual gas to be measured, contained in the sample gas based on a detection signal value obtained from the photodetector. The operation device calculates the concentration of the actual gas based on a function $\alpha$ for associating a concentration of a substitute gas with a concentration of the actual gas that are both obtained from a reference instrument that is an individual instrument body serving as a reference, a function $\beta$ for associating a relation of a light absorption of the actual gas with a light absorption of the substitute gas in the reference instrument, with a relation between a light absorption of the actual gas and a light absorption of the substitute gas in a calibration instrument that is an individual instrument body to be calibrated, and a function indicating a relation between the concentration of the substitute gas and the detection signal value from the calibration instrument.

Specifically, such a spectrophotometer includes a non-dispersive infrared spectrophotometer.

In another aspect of the invention, a method of calibrating a spectrophotometer is provided. That is, the method of calibrating the spectrophotometer, including a light source for irradiating light into a sample gas, a photodetector for detecting light transmitted through the sample gas, an optical filter arranged between the light source and the photodetector, and an operation device for calculating a concentration of an actual gas to be measured, contained in the sample gas based on a detection signal value obtained from the photodetector, includes obtaining a function $\alpha$ for associating a concentration of a substitute gas with a concentration of the actual gas that are obtained from a reference instrument that is an individual instrument body serving as a reference, obtaining a function β for associating a relation between a light absorption of the actual gas and a light absorption of the substitute gas in the reference instrument, with a relation between a light absorption of the actual gas and a light absorption of the substitute gas in a calibration instrument that is an individual instrument body to be calibrated, obtaining a function indicating a relation between the concentration of the substitute gas and the detection signal value for the calibration instrument, and calculating the concentration of the actual gas based on the functions.

Thus, according to the present invention, an instrumental difference of the ratio in infrared light absorption between the actual gas and the substitute gas (abs.$_{actual\_gasactual\_gas}$/abs.$_{substitute\_gas}$), due to a difference in optical property of the optical filter, can be eliminated, and therefore, a stable and highly accurate analysis can be performed.

DETAILED DESCRIPTION OF THE EMBODIMENTS

Hereinafter, an embodiment of the present invention is described in detail with reference to the appended drawings.

Figure 1:
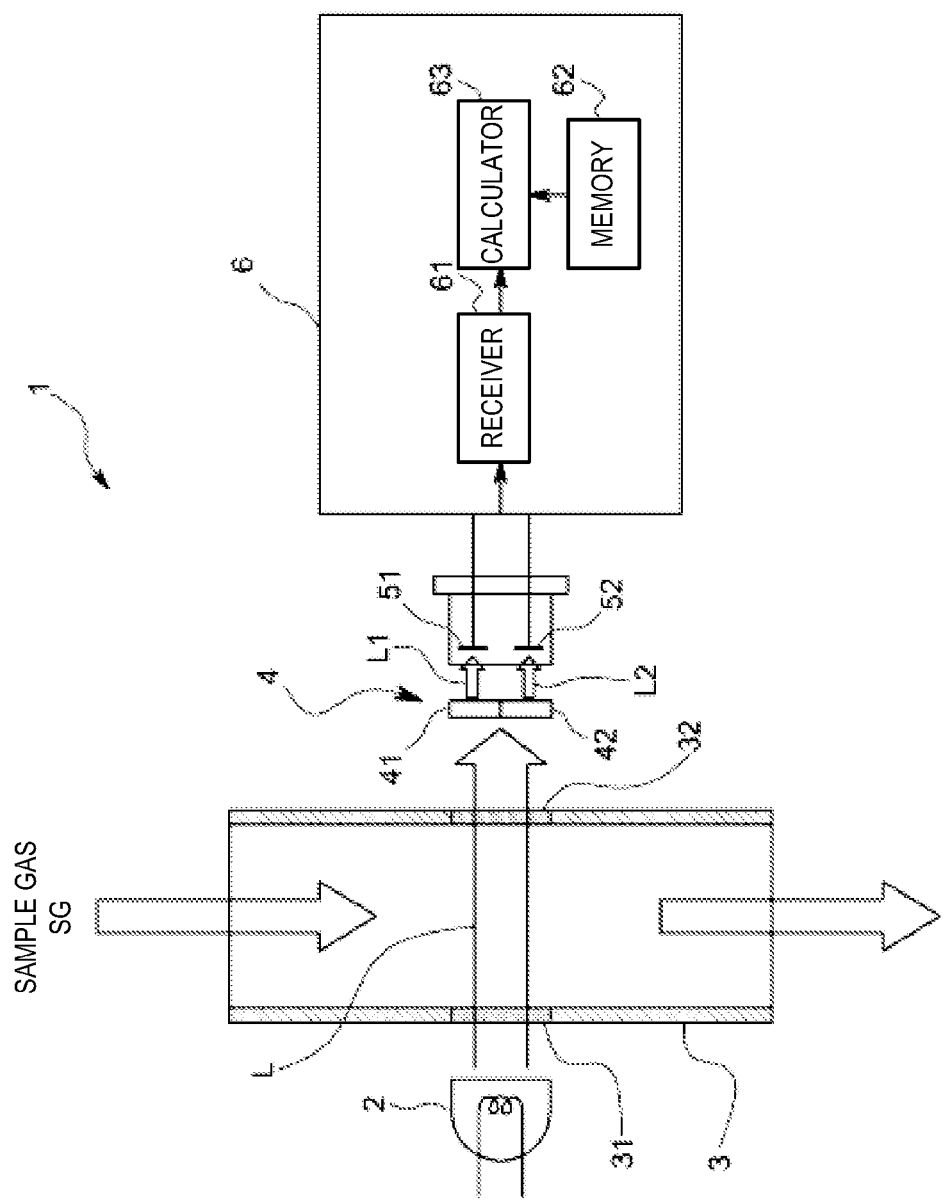
FIG. 1 is a configuration diagram of an NDIR according to an embodiment of the invention.

As shown in FIG. 1, a non-dispersive infrared spectrophotometer (NDIR) 1 according to this embodiment includes a light source 2, a measurement cell 3, an optical filter 4, a pair of photodetectors 51 and 52, and an operation device 6.

Hereinafter, each component is explained. The light source 2 is a candescent type that produces luminescence by heating, for example, a filament. The light source 2 includes one source and irradiates a light L with a broad band range having a measurement light L1 that attenuates when being irradiated to and absorbed by an actual gas and a reference light L2 that substantially does not attenuate even when being irradiated to the actual gas.

The measurement cell 3 is a flow type having a cylinder shape opened at both ends. A sample gas SG containing the actual gas that is a measurement target is led into the measurement cell 3 from an opening at one end thereof and led out thereof from an opening at the other end, so that the sample gas SG flows through inside the measurement cell 3 in an axial direction. Further, in parts of a wall body of the measurement cell 3 opposite to each other, a light entry window 31 and a light exit window 32 that are sealed with an infrared transmission optical crystal, such as sapphire, are respectively formed so that the light L can be transmitted from outside the cell in a direction orthogonal to the axial direction (direction of the gas flow), via the windows 31 and 32.

The optical filter 4 has a thin plate shape, and is configured with a first bandpass filter 41 that occupies a half of the range of the optical filter and for only transmitting the measurement light L1, and configured with a second bandpass filter 42 that occupies the rest of the range of the optical filter and for only transmitting the reference light L2.

Pyrosensors using a pyroelectric effect, which are heating-type infrared ray sensors, are used as the pair of photodetectors 51 and 52. One of the sensors, that is the photodetector 51 is provided to face the first bandpass filter 41 and the other sensor, that is the photodetector 52 is provided to face the second bandpass filter 42, the photodetector 51 receives the measurement light L1 and the reference light L2 passed through the bandpass filter 41 and the photodetector 52 receives the measurement light L1 and the reference light L2 passed through the bandpass filter 42, and the photodetectors 51 and 52 output electric signal values to the operation device 6 according to a received light volume.

The operation device 6 acquires the photo detection signals obtained from the photodetectors 51 and 52, and calculates, for example, a concentration of the actual gas contained within the sample gas SG based on the values of the photo detection signals. Note that, such photo detection signal values include, for example, voltage values and current values generated by the photodetectors 51 and 52, and values of light absorption and transmittance detected by the photodetectors 51 and 52; however, without limitation to these, they may be values derived by performing, for example, a predetermined correction or operation processing on the above values.

The operation device 6 is, specifically, configured with a digital circuit having, for example, a CPU, memory, an A/D converter, and a D/A converter, and/or an analog electric circuit, and may be a dedicated device or may use a general-use computer, such as a personal computer, in part or entirely. Alternatively, the operation device 6 may fulfill the function of each of the above components by analog circuits only, without utilizing a CPU, or, since it is not necessarily physically a single device, may be constituted with a plurality of equipments connected to each other by or without fixed line(s).

Further, by storing a predetermined program in the memory and cooperatively operating the CPU and peripheral equipments according to the program, the operation device 6 is configured to perform functions as, for example, a receiver 61 for receiving the photo detection signals detected by the photodetectors 51 and 52, memory 62 for storing a calculation equation ($C_{actual\_gasactual\_gas} = \alpha \times f_{calibration\_instrument}(\beta \times x)$) for the actual gas concentration $C_{actual\_gasactual\_gas}$, in which a variable x is derived from the photo detection signal values, and a calculator 63 for acquiring the photo detection signal values from the receiver 61, as well as acquiring the equation from the memory 62 and calculating the actual gas concentration $C_{actual\_gasactual\_gas}$ contained within the sample gas SG.

The equation for the actual gas concentration $C_{actual\_gasactual\_gas}$ ($C_{actual\_gasactual\_gas} = \alpha \times f_{calibration\_instrument}(\beta \times x)$) is stored in the operation device 6 when the initial concentration calibration is performed for the NDIR 1.

Figure 2:
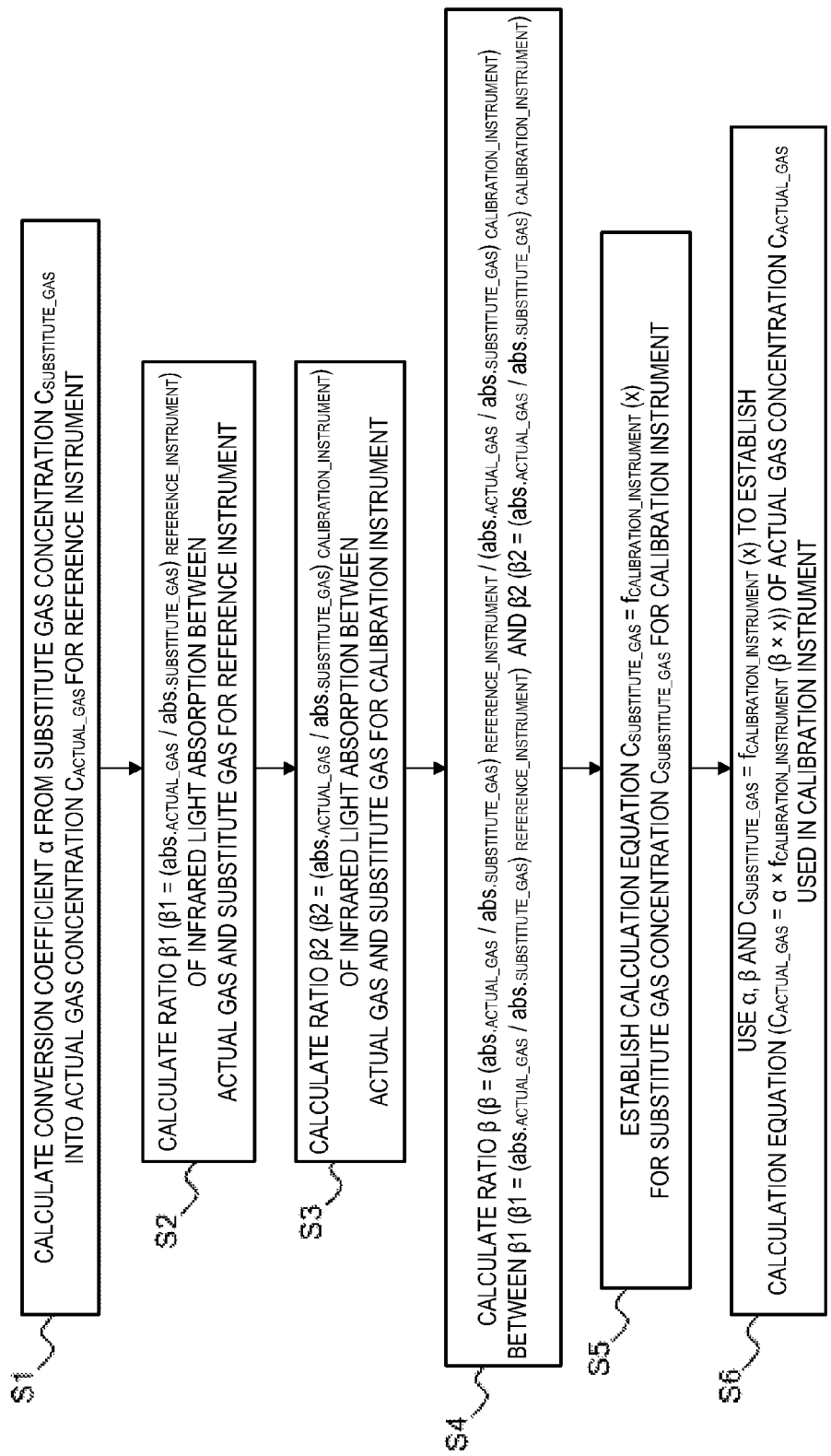
FIG. 2 is a flowchart showing a procedure of calibrating the NDIR of the embodiment.

The equation for the actual gas concentration $C_{actual\_gasactual\_gas}$ ($C_{actual\_gasactual\_gas} = \alpha \times f_{calibration\_instrument}(\beta \times x)$) is established based on the procedure shown in FIG. 2. That is, first, a reference instrument that is an individual instrument body to serve as a reference is selected among NDIRs with the same specification, and with this reference instrument, the actual gas that is the measurement target is released into the measurement cell 3 of the reference instrument, and an equation expressing a relation between the actual gas concentration $C_{actual\_gasactual\_gas}$ and the photo detection signal values x, obtained from the photodetectors 51 and 52, is obtained ($C_{actual\_gasactual\_gas} = g_{reference\_instrument}$ (x)). Further, the actual gas is changed to a substitute gas, and an equation similarly expressing a relation between a substitute gas concentration $C_{substitute\_gas}$ and the photo detection signal values x obtained from the photodetectors 51 and 52 is obtained ($C_{substitute\_gas} = f_{reference\_instrument}$ (x)). Thus, based on these equations, a conversion coefficient α with which the substitute gas concentration $C_{substitute\_gas}$ is converted into the actual gas concentration $C_{actual\_gasactual\_gas}$ is obtained (Step S1).

Note that, the conversion coefficient α may be obtained by introducing the actual gas and the substitute gas into the reference instrument respectively, setting the substitute gas concentration $C_{substitute\_gas}$ and the actual gas concentration $C_{actual\_gasactual\_gas}$ with which the photo detection signal values x obtained from the photodetectors 51 and 52 matched with each other as a pair, and plotting (the substitute gas concentration $C_{substitute\_gas}$, the actual gas concentration $C_{actual\_gasactual\_gas}$) obtained for a plurality of photo detection signal values on an x-y coordinate.

Note that, the reference instrument indicates either one of a representative NDIR among the NDIR with the same specification (same standards of, for example, the light source 2, the measurement cell 3, the optical filter 4, and the photodetectors 51 and 52, that is, they have the same configuration; however, each instrument is different due to, for example, mechanical tolerances) and a certain NDIR arbitrarily selected as an average NDIR. Specifically, the reference instrument indicates an instrument body that is introduced with the actual gas and is used to obtain the equation expressing the relation between the actual gas concentration $C_{actual\_gas}$ and the photo detection signal values x, obtained from the photodetectors ($C_{actual\_gas} = g_{reference\_instrument}$ (x)), and as long as it is a separate instrument body from a calibration instrument and can be used to obtain $C_{actual\_gas} = g_{reference\_instrument}$ (x), any instrument body may serve as the reference instrument.

Figure 4:
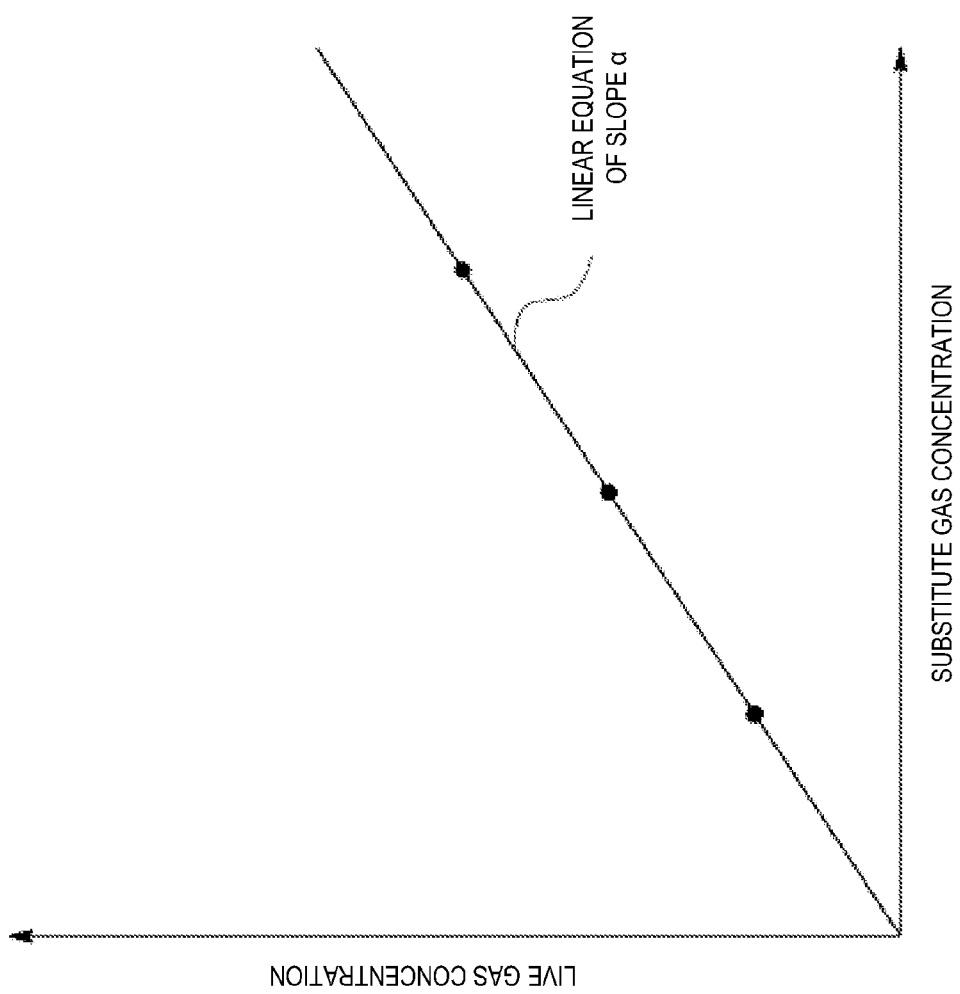
FIG. 4 is a chart showing a relation in concentration between an actual gas and a substitute gas.
Figure 5:
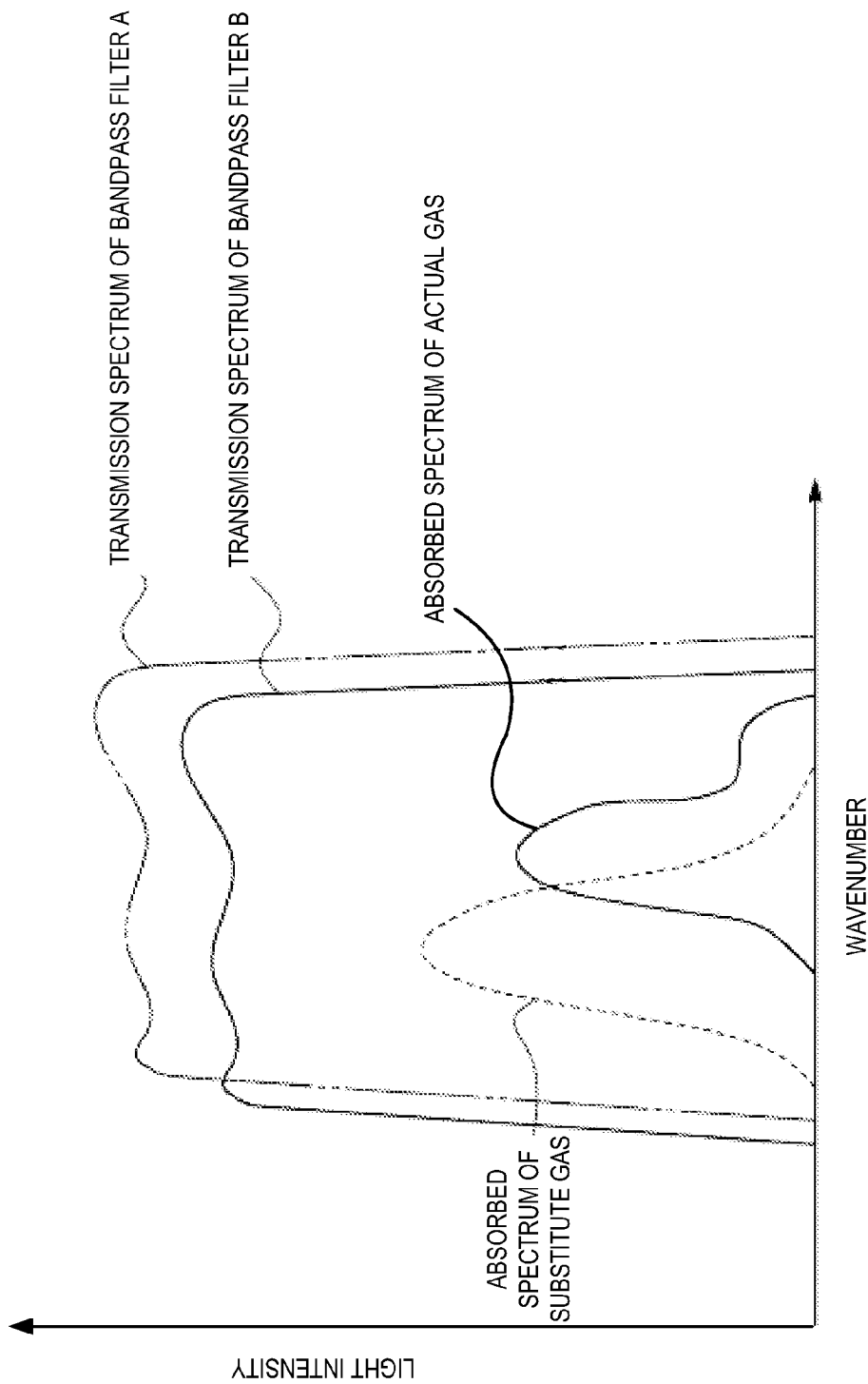
FIG. 5 is a chart showing an instrumental difference in transmission spectrum of bandpass filters.

Further, in this embodiment, although, the substitute gas concentration $C_{substitute\_gas}$ and the actual gas concentration $C_{actual\_gas}$ are, as shown in FIG. 4, in a relation that is expressed in a linear equation having the slope α, the conversion coefficient α varies based on the kinds of the substitute gas and the actual gas and is not limited to the slope of the linear equation.

Next, with the reference instrument, a ratio β1 in infrared light absorption between the actual gas and the substitute gas (β1=(abs.$_{actual\_gas}$/abs.$_{substitute\_gas}$)$_{reference\_instrument}$) is calculated (Step S2).

Note that, the infrared light absorption of the actual gas (abs.$_{actual\_gas}$) and the infrared light absorption of the substitute gas (abs.$_{substitute\_gas}$) with the reference instrument are calculated through releasing the actual gas and the substitute gas of the reference instrument individually to the measurement cell 3 to measure each light intensity $I_x$ thereof and comparing the light intensity $I_x$ with a light intensity $I_o$ of when neither of the gases is released, according to an equation: abs.$=(I_o-I_x)/I_o$.

Figure 3:
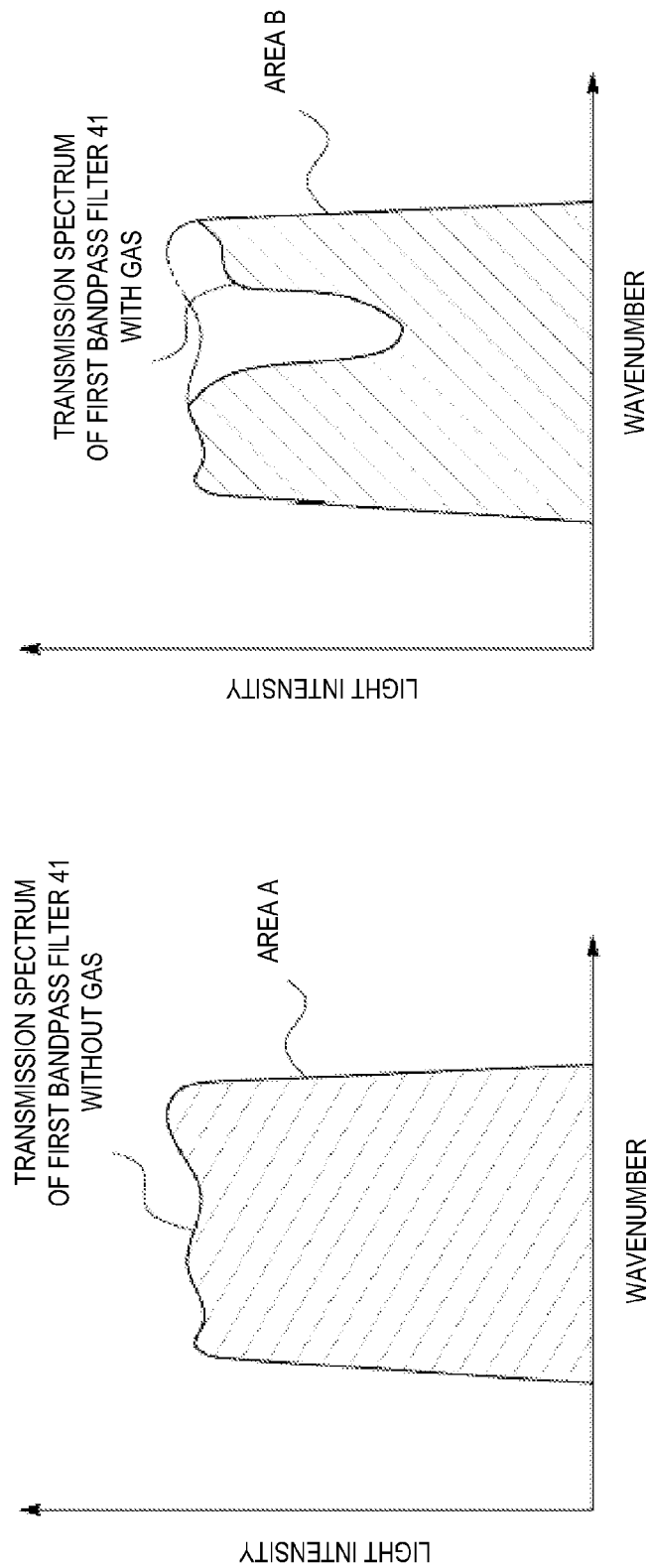
FIGS. 3A and 3B are charts showing transmission spectrums of a first bandpass filter of the embodiment.

Further, for the calibration instrument (the NDIR 1 in this embodiment) that is a single instrument body to be calibrated, a ratio β2 in infrared light absorption between the actual gas and the substitute gas (β2=(abs.$_{actual\_gas}$/abs.$_{substitute\_gas}$)$_{calibration\_instrument}$) is calculated (Step S3). Here, the infrared light absorption of the actual gas (abs.$_{actual\_gas}$) and the infrared light absorption of the substitute gas (abs.$_{substitute\_gas}$) with the calibration instrument can be calculated with 1−(B/A) through obtaining an area A and an area B according to a transmission spectrum of the first bandpass filter 41 measured in advance by using a spectrophotometer such as an FTIR, and a transmission spectrum of either one of the actual gas and the substitute gas measured in advance with the reference instrument or a transmission spectrum of either one of the actual gas and the substitute gas which are described in, for example, JP2000-241346A or JP2005-257358A, as shown in FIGS. 3A and 3B. Specifically, according to a transmittance Tr$_{filter}$ of the first bandpass filter 41 and a transmittance Tr$_{actual\_gas\ (or\ substitute\_gas)}$ of the actual gas (or substitute gas), the infrared light absorptivities of the actual gas and the substitute gas can be obtained based on a relational equation: abs.$_{actual\_gas\ (or\ substitute\_gas)}=1-\{\int(Tr_{filter} \times Tr_{actual\_gas\ (or\ substitute\_gas)})/\int(Tr_{filter})\}$.

Note that, the infrared light absorption (abs.$_{substitute\_gas}$) of the substitute gas with the calibration instrument may be calculated through releasing the substitute gas to the measurement cell 3 of the calibration instrument to measure the light intensity $I_x$ thereof and comparing the light intensity $I_x$ with the light intensity $I_o$ of when the substitute gas is not released, according to the equation: abs.$=(I_o-I_x)/I_o$.

Next, a ratio β=(abs.$_{actual\_gas}$/abs.$_{substitute\_gas}$)$_{reference\_instrument}$)/(abs.$_{actual\_gas}$/abs.$_{substitute\_gas}$)$_{calibration\_instrument}$) between β1 (β1=(abs.$_{actual\_gas}$/abs.$_{substitute\_gas}$)$_{reference\_instrument}$) and β2 (β2=(abs.$_{actual\_gas}$/abs.$_{substitute\_gas}$)$_{calibration\_instrument}$) is calculated (Step S4).

Further, with the calibration instrument, the substitute gas in which the concentration is known is released to the measurement cell 3, a relation between the photo detection signal values obtained from the photodetectors 51 and 52 and the substitute gas concentration is examined, and a function of the substitute gas concentration $C_{substitute\_gas}$ (the calculation equation for the substitute gas concentration $C_{substitute\_gas}$; $C_{substitute\_gas} = f_{calibration\_instrument}$ (x)), in which the variable x is derived from the photo detection signal values, is established (Step S5).

Finally, the α is applied as the coefficient for the conversion of the substitute gas into the actual gas and the β is applied as the coefficient for the conversion of the calibration instrument into the reference instrument. By using these conversion coefficients, based on the calculation equation for the substitute gas concentration $C_{substitute\_gas}$ ($C_{substitute\_gas} = f_{calibration\_instrument}$ (x)), the calculation equation for the actual gas concentration $C_{actual\_gas}$ used in the calibration instrument ($C_{actual\_gas} = \alpha \times f_{calibration\_instrument}$ (β×x)) is established (Step S6).

The value of the actual gas concentration calculated by the operation device 6 is outputted to, for example, a display and a recording device.

Therefore, according to the NDIR 1 of this embodiment configured as above, an instrumental difference of the ratio in infrared light absorption between the actual gas and the substitute gas (abs.$_{actual\_gas}$/abs.$_{substitute\_gas}$) due to the difference in optical property of bandpass filters can be eliminated, and even when the actual gas concentration in the calibration instrument is measured, the same result as when the measurement is performed for the reference instrument can be obtained, therefore, a stable and highly accurate analysis can be performed. Note that, in the above embodiment, although the calibration and the determination of the value for β are performed based on the infrared light absorption, alternative to the infrared light absorption, for example, the voltage values and current values generated by the photodetectors 51 and 52, and the values of the light absorption and the transmittance detected by the photodetectors 51 and 52 may be used.

Note that, the present invention is not limited to the above embodiment. Hereinafter, modified embodiments are described.

For example, the spectrophotometer used in the invention is not limited to the NDIR, and may be any others as long as an optical filter is included therein, for example, the present invention can be applied to a non-dispersive ultraviolet spectrophotometer (NDUV).

Figure 6:
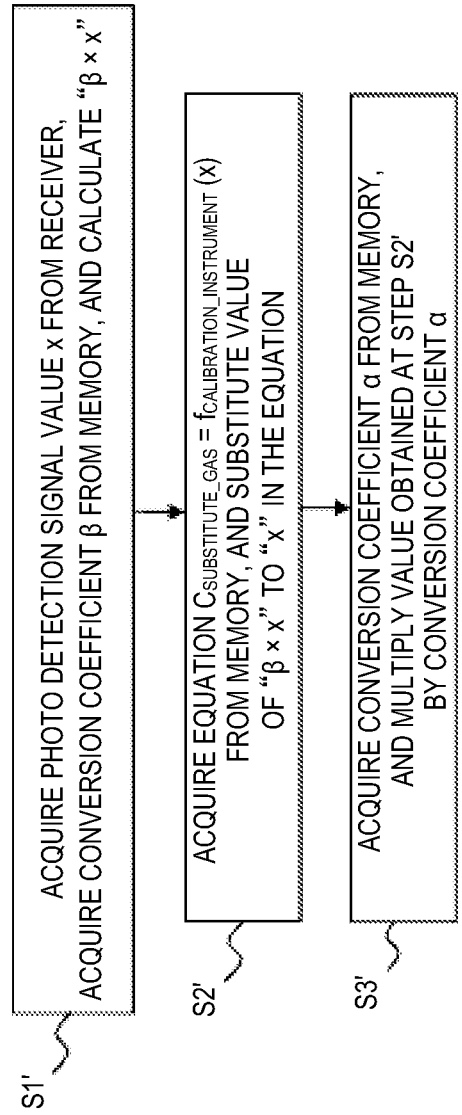
FIG. 6 is a flowchart showing a procedure of calculating a concentration of an actual gas of another embodiment.

Further, in the above embodiment, although the calculation equation for the actual gas concentration $C_{actual\_gas}$, in which the variable x is derived from the photo detection signal values, ($C_{actual\_gas} = \alpha \times f_{calibration\_instrument}(\beta \times x)$) is stored in the memory 62 and the calculator 63 calculates the actual gas concentration $C_{actual\_gas}$ within the sample gas SG based on the calculation equation, the method of calculating the actual gas concentration $C_{actual\_gas}$ is not limited to this, and, for example, the memory 62 may store an equation $C_{substitute\_gas} = f_{calibration\_instrument}(x)$, the conversion variables $\alpha$ and $\beta$ in advance, and the calculator 63 may perform operation processing in a predetermined order based on the equation $C_{substitute\_gas} = f_{calibration\_instrument}(x)$, and conversion variables $\alpha$ and $\beta$, as shown in FIG. 6. Further alternatively, various manners can be considered as the method of calculating the actual gas concentration $C_{actual\_gas}$ within the sample gas SG, for example, the actual gas concentration $C_{actual\_gas}$ within the sample gas SG may be calculated by using, for example, a composed function of the conversion coefficients $\alpha$ and $\beta$, or a composed function of $\alpha$ or $\beta$, and $f_{calibration\_instrument}(x)$. Further, the performance order of each process shown in FIG. 6 may be suitably changed, and moreover, for example, the composed function of the conversion coefficients $\alpha$ and $\beta$, or the composed function of $\alpha$ or $\beta$, and $f_{calibration\_instrument}(x)$ may be used for any one of the process of the operation processing by the calculator 63 as illustratively shown in FIG. 6.

Furthermore, in the present invention, the above embodiment and the modified embodiments may suitably be combined partially or entirely, and naturally, other various kinds of modifications may be applied within a range of not deviating from the spirit and scope of the present invention.

DESCRIPTION OF REFERENCE NUMERALS

1 NDIR
2 Light Source
4 Optical Filter
51, 52 Photodetector
100 Operation Device

The invention claimed is:

1. A spectrophotometer, comprising:
a light source for irradiating light into a sample gas;
a photodetector for detecting light transmitted through the sample gas;
an optical filter arranged between the light source and the photodetector; and
an operation device for calculating a concentration of an actual gas to be measured, contained in the sample gas based on a detection signal value obtained from the photodetector,
wherein the operation device calculates the concentration of the actual gas based on a function $\alpha$ for associating a concentration of a substitute gas with a concentration of the actual gas that are obtained from a reference instrument that is an individual instrument body serving as a reference, a function $\beta$ for associating a relation between a light absorption of the actual gas and a light absorption of the substitute gas in the reference instrument, with a relation between the light absorption of the actual gas and the light absorption of the substitute gas in a calibration instrument that is an individual instrument body to be calibrated, and a function indicating a relation between the concentration of the substitute gas and the detection signal value from the calibration instrument.

2. The spectrophotometer of claim 1, wherein the spectrophotometer is a non-dispersive infrared spectrophotometer.

3. A method of calibrating a spectrophotometer, comprising:
a light source for irradiating light into a sample gas, a photodetector for detecting light transmitted through the sample gas, an optical filter arranged between the light source and the photodetector, and an operation device for calculating a concentration of an actual gas to be measured, contained in the sample gas based on a detection signal value obtained from the photodetector, the method comprising:
obtaining a function $\alpha$ for associating a concentration of a substitute gas with the concentration of the actual gas that are obtained from a reference instrument that is an individual instrument body serving as a reference;
obtaining a function $\beta$ for associating a relation between a light absorption of the actual gas and a light absorption of the substitute gas in the reference instrument, with a relation between the light absorption of the actual gas and the light absorption of the substitute gas in a calibration instrument that is an individual instrument body to be calibrated;
obtaining a function indicating a relation between the concentration of the substitute gas and the detection signal value for the calibration instrument; and
calculating the concentration of the actual gas based on the functions.

* * * * *